United States Patent [19]

Rapoport

[11] 4,328,172
[45] May 4, 1982

[54] HYDROCYANATION OF OLEFINS

[75] Inventor: Morris Rapoport, Orange, Tex.

[73] Assignee: E. I. Du Pont de Nemours and Company, Wilmington, Del.

[21] Appl. No.: 237,613

[22] Filed: Feb. 24, 1981

[51] Int. Cl.$^3$ .................. C07C 120/02; C07C 121/26
[52] U.S. Cl. ............................................. 260/465.8 R
[58] Field of Search ................................. 260/465.8 R

[56] References Cited

U.S. PATENT DOCUMENTS

| | | | |
|---|---|---|---|
| 3,496,218 | 2/1970 | Drinkard, Jr. | 260/465.3 X |
| 3,766,237 | 10/1973 | Chia et al. | 260/465.3 |
| 3,903,120 | 9/1975 | Shook, Jr. et al. | 260/346.74 X |
| 4,080,374 | 3/1978 | Corn | 260/465.3 |
| 4,082,811 | 4/1978 | Shook, Jr. | 260/465.9 X |

Primary Examiner—Joseph Paul Brust

[57] ABSTRACT

An improved process for the production of dinitriles, e.g., adiponitrile, by the hydrocyanation of 3 and/or 4-pentenenitriles by staging the introduction of hydrogen cyanide to the reaction.

6 Claims, No Drawings

HYDROCYANATION OF OLEFINS

BACKGROUND OF THE INVENTION

1. Field of the Invention

The present process is directed to the production of dinitriles and more particularly, to the production of adiponitrile by the hydrocyanation of 3- and/or 4-pentenenitriles in the presence of a zero-valent nickel catalyst promoted by an organoborane.

2. Description of the Prior Art

U.S. Pat. No. 3,496,218 issued on Feb. 17, 1970 describes in general terms a process for the preparation of dinitriles especially adiponitrile by the hydrocyanation of non-conjugated, ethylenically unsaturated organic compounds, e.g., 3- and/or 4-pentenenitriles using certain nickel complexes as catalysts. The catalysts are promoted by organoborane compounds such as triphenylborane. A wide range of process conditions and relative amounts and types of reactants are disclosed.

A particularly useful form of zero-valent nickel catalyst is described in U.S. Pat. No. 3,766,237 issued on Oct. 16, 1973. The patentees disclose the use of an excess of the triarylphosphite ligand in the hydrocyanation along with the addition of certain ethers to improve the yield and increase the pounds of product which can be made per pound of catalyst consumed.

U.S. Pat. No. 4,082,811 issued on Apr. 4, 1978 discloses a hydrocyanation process coupled with a method for recovery of catalyst.

SUMMARY OF THE INVENTION

A method for reducing the amount of promoter required in a continuous process for the production of dinitriles, e.g., adiponitrile by the addition of hydrogen cyanide to non-conjugated, ethylenically unsaturated nitriles, e.g., 4-pentenenitrile using a zero-valent nickel catalyst promoted with an organoborane such as triphenylborane, which comprises conducting the process in at least two successive stages with the effluent from one stage being directed to the next stage, introducing hydrogen cyanide into said stages in an amount such that at least 10%, and preferably at least 15%, by weight of the total hydrogen cyanide fed is introduced into each stage.

In one preferred embodiment, a greater amount of hydrogen cyanide is fed to the initial stages relative to subsequent stages and the temperature in the initial stage is maintained below that in subsequent stages.

DETAILED DESCRIPTION OF THE INVENTION

The reactants, catalyst and promoter to which the present invention is applicable are described generally in U.S. Pat. No. 3,496,218 issued on Feb. 17, 1970 to Drinkard et al which disclosure is incorporated herein by this reference.

The present invention can be employed to produce a variety of dinitriles but adiponitrile (ADN) is of particular interest because it is an intermediate used in the production of hexamethylene-diamine which in turn is used to produce polyhexamethyleneadipamide, a commercial polyamide useful in forming fibers, films and molded articles.

The hydrocyanation reaction can employ any non-conjugated, ethylenically unsaturated organic nitrile of from 4 to 20 carbon atoms. It is of particular interest in the hydrocyanation of pentenenitriles, e.g., cis- and trans-3- pentenenitrile (3PN), 4-pentenenitrile (4PN) and mixtures thereof (3,4-PN's).

The preparation of zero-valent nickel (Ni$^o$) catalyst which is used in the practice of the present invention is found in U.S. Pat. No. 3,903,120 issued on Sept. 2, 1975. Preferred catalysts are those having the general formula NiL$_4$ where L is a neutral ligand such as a triarylphosphite of the formula P(OAr)$_3$ wherein Ar is an aryl group of up to 18 carbon atoms. Illustrative of the aryl groups are methoxyphenyl, tolyl, xylyl and phenyl. Meta- and para-tolyl and mixtures thereof are the preferred aryl groups. Excess ligand can be employed.

The promoters which are used with the above-described catalyst are triarylboranes including those of the formula BR$_3$ wherein R is an aryl or a substituted aryl group having 6 to 12 carbon atoms, e.g., phenyl, ortho-tolyl, para-tolyl, napthyl, methoxyphenyl, biphenyl, chlorophenyl and bromophenyl. Triphenylborane (TPB) is preferred.

The following discussion is directed to the hydrocyanation of 3PN and/or 4PN to produce ADN using Ni$^o$ catalyst containing a mixed m,p-tritolyl phosphite ligand with a triphenylborane (TPB) promoter, but applies to other types of nitriles and catalysts as described above.

The present process can be conducted in at least two and, preferably, continuously in at least three immediately successive stages. The stages are arranged in series with the effluent from an initial stage being directed to the next or subsequent stage. The hydrogen cyanide is introduced in two or more stages. For purposes of the present invention a stage is defined as a zone where at least 10%, and preferably, at least 15% of the total hydrogen cyanide fed is introduced and substantially reacted. Substantially reacted means that at least 70%, usually at least 80%, and preferably, at least 90% of the hydrogen cyanide is reacted. In an especially preferred mode in the initial stage(s) greater than 95% of the hydrogen cyanide introduced is reacted. Equal amounts of hydrogen cyanide can be introduced into each stage or varying amounts can be introduced. It is not necessary to introduce hydrogen cyanide into each zone in a series of zones but only those zones into which hydrogen cyanide is introduced and substantially reacted are considered to be stages for purposes of the present invention. In a preferred embodiment a greater amount of hydrogen cyanide is introduced into the initial stages relative to the subsequent stages.

The arrangement and design of the stages is not critical to the present invention. The staging can be accomplished in a series of conventional stirred reactors as described in the Examples. An alternate apparatus to accomplish staging could be a tower reactor wherein the stages are vertically positioned with the effluent from one stage flowing to the next stage and hydrogen cyanide being introduced into each stage. The stages need not be physically separated but may be identified by a plurality of locations where hydrogen cyanide is introduced and the reaction permitted to be substantially completed before the next point of introduction of the hydrogen cyanide. Other devices, e.g., staged tubular reactors should be apparent to those skilled in the art.

The reaction conditions can vary from stage to stage but the temperature of the reaction should usually not be below 25° C. to produce adiponitrile in an acceptable yield at a commercially feasible rate. At temperatures above 75° C., e.g., 100° C., it has been found that the yield loss is excessive and that no commercially practical adjustments in the reactants or other reaction variables can be made to duplicate performance at lower temperatures. It is preferred to maintain the temperature in the initial stage(s) below the temperature in subsequent stages.

The benefits from staging are two fold. The most striking is the fact that the amount of promoter necessary to sustain a satisfactory reaction may be lowered substantially, e.g., by as much as 65% without other penalties to result in more economical operation. Another surprising benefit is that temperature of the reaction optionally can be concurrently reduced and the rate increased, with the resultant reduction in the yield loss to 2-pentenenitriles.

The following Examples and Comparative are presented to illustrate but not to restrict the present invention. Parts and percentages are by weight unless otherwise noted. The following abbreviations and definitions are used in the Examples:

TTP = the reaction product of $PCl_3$ and commercially available m,p-cresol which contains minor amounts of related phenols.

$$\text{Conversion} = \frac{\text{mols of 3- and 4-PN's consumed}}{\text{mols of 3- and 4-PN's fed}} \times 100$$

$$\text{Yield (ADN)} = \frac{\text{mols of ADN produced}}{\text{mols of 3- and 4-PN's consumed}} \times 100$$

$$\text{Yield (2PN)} = \frac{\text{mols of 2-PN produced}}{\text{mols of 3- and 4-PN's consumed}} \times 100$$

The apparatus employed in all the Examples consisted of 1, 2, or 3 glass flasks as reactors of approximately 25 cc in volume which when more than one reactor was employed were connected in series with the overflow from the first reactor directed by gravity to the second reactor and the overflow from the second reactor directed by gravity to the third reactor. Overflow from the last reactor was retained in a product receiver which was periodically changed. Each reactor was equipped with an individually controlled electrical heating means and side arms for sampling the contents during the course of a run. The first reactor was provided with an inlet port for catalyst solution, promoter solution and pentenenitriles. Each reactor was equipped with a port for introductions of hydrogen cyanide below the liquid contents of the flasks. A nitrogen inlet was provided to the vapor space of each reactor and the product receiver to provide a non-oxidizing atmosphere. The pentenenitriles introduced to the reactor and used to prepare the solutions described hereinbelow contained about 98% 3PN and 1% 4PN with trace amounts of other nitriles. Pentenenitriles of lessor purity can be used with essentially similar results. Catalyst solution which was introduced into the first reactor was prepared by reacting a mixture containing 77% TTP, 20% PN's, 3% nickel powder, to which mixture had been added 100 ppm chloride catalyst as phophorous trichloride. The mixture was heated for 16 hours at 80° C., cooled and filtered to yield a solution containing approximately 2.7% by weight zero-valent nickel ($Ni^0$). The promoter solution was prepared by dissolving a mixture of dry TPB in the above-described nitriles to yield a solution containing about 20% by weight TPB. Hydrogen cyanide employed in the examples was essentially free of sulfuric acid and contained only trace amounts of sulfur dioxide. The hydrogen cyanide was cooled to about 0° C. to prevent degradation prior to introduction in the first stage (or stages). The system was started up by adding catalyst solution, pentenenitriles and promoter solution to each reactor at room temperature. Agitation was then started. After warming the reactor(s) to the indicated temperature introduction of hydrogen cyanide was commenced. When the reaction reached steady state as shown by a constant concentration of hydrogen cyanide in the reaction medium at a level indicating substantial reaction of HCN, samples of the reactor contents and products were withdrawn and analyzed by gas chromatographic analysis to determine the amount of ADN, 3PN, 4PN and 2PN which were present therein. Failure to achieve a constant concentration of hydrogen cyanide with substantial reaction of HCN indicates that the reaction is not operating satisfactorily.

Comparative

A single stage hydrocyanation was conducted according to the above-described procedure. The feed ratios and results at steady state operation are given in the Table.

The above was repeated except that the TPB/HCN ratio was reduced to 0.005 (about 50% of that used initially). The system would not reach steady state. The level of promoter was insufficient to provide an operative system.

EXAMPLE I

A two stage hydrocyanation was conducted using two flasks arranged and operated according to the above-described procedure. The feed ratios, the split of HCN to each stage, and results are given in the Table. Satisfactory operation was achieved at a TPB level of about 60% of that of the comparative even though the rate was nearly twice as rapid.

EXAMPLE II

A three stage hydrocyanation was conducted using three flasks arranged and operated according to the above-described procedure. The feed ratios, split of HCN to each stage and results are given in the Table. The TPB and HCN ratio was 0.0034 or approximately one third of that of the comparative Operation was satisfactory in all respects.

TABLE

| Example No. | FEED (Mol Ratio Based Upon Mol Of $Ni^0$) | | | | Mol Ratio of $\frac{TPB}{HCN}$ | Weight % $Ni^0$ | TEMPERATURE (°C.) By Stage | | | HCN SPLIT (% By Weight) By Stage | | | OVERALL RATE gms ADN/ cc/min $\times 10^4$ | CONVERSION (%) | YIELD ADN (%) | YIELD 2PN (%) |
|---|---|---|---|---|---|---|---|---|---|---|---|---|---|---|---|---|
| | TPB | TTP | 3,4-PN's | HCN | | | 1st | 2nd | 3rd | 1st | 2nd | 3rd | | | | |
| Compara- TABLE-continued

| Example No. | FEED (Mol Ratio Based Upon Mol Of Ni°) | | | | Mol Ratio of TPB/HCN | Weight % Ni° | TEMPERATURE (°C.) By Stage | | | HCN SPLIT (% By Weight) By Stage | | | OVERALL RATE gms ADN/ cc/min × 10⁴ | CONVERSION (%) | YIELD ADN (%) | YIELD 2PN (%) |
|---|---|---|---|---|---|---|---|---|---|---|---|---|---|---|---|---|
| | TPB | TTP | 3,4-PN's | HCN | | | 1st | 2nd | 3rd | 1st | 2nd | 3rd | | | | |
| tive | .488 | 8.59 | 101.4 | 49.5 | 0.0099 | 0.451 | 50 | — | — | 100 | — | — | 2.78 | 50.3 | 93.0 | 3.5 |
| 1 | 0.229 | 7.54 | 92.8[1] | 38.6 | 0.0059 | 0.489 | 35 | 55 | — | 60.3 | 39.7 | — | 5.39 | 40.6 | 94.2 | 2.8 |
| 2 | 0.172 | 8.03 | 103.5[2] | 50.2 | 0.0034 | 0.443 | 40 | 45 | 50 | 46.1 | 30.2 | 23.7 | 2.64 | 46.1 | 94.1 | 2.5 |

[1] One part of regular 3PN and 4PN feed was combined with about one part of a stream containing about 70% 3PN and 4PN, about 10% 2PN, about 12% 2-methyl-2-butenenitrile and 8% valeronitrile

[2] As in footnote 1 except that 1.3 parts of regular feed was combined with 1 part of the stream

I claim:

1. In a continuous process for the production of dinitriles by the addition of hydrogen cyanide to non-conjugated, unsaturated nitriles in the presence of a zero-valent nickel catalyst promoted with at least one arylborane, a method for reducing the level of promoter required to sustain a rapid reaction rate which comprises conducting the process in at least two immediately successive stages with the effluent from one stage being directed to the next stage, introducing hydrogen cyanide into said stages in an amount such that at least 10% by weight of the total hydrogen cyanide fed is introduced into each stage.

2. The process of claim 1 wherein a greater amount of hydrogen cyanide is fed to the initial stages relative to subsequent stages.

3. The process of claim 2 wherein the temperature in the initial stages is maintained below that in subsequent stages.

4. The process of claim 1 wherein at least 15% by weight of the total hydrogen cyanide fed is introduced into each stage.

5. The process of claims 1, 2, 3, or 4 wherein the dinitrile is adiponitrile, the zero-valent nickel catalyst is defined by the formula $NiL_4$ where L is $P(OAr)_3$ and Ar is an aryl group of up to 18 carbon atoms and the arylborane is defined by the formula $BR_3$ where R is an aryl group having 6-12 carbon atoms.

6. The process of claim 5 wherein the arylborane is triphenylborane.

* * * * *